(12) United States Patent
Herve

(10) Patent No.: US 7,090,505 B2
(45) Date of Patent: Aug. 15, 2006

(54) CONNECTING METHOD FOR STRUCTURE WITH IMPLANTABLE ELECTRODES

(75) Inventor: Thierry Herve, Le Sappey en Chartreuse (FR)

(73) Assignee: Microvitae Technologies, Corenc (FR)

( * ) Notice: Subject to any disclaimer, the term of this patent is extended or adjusted under 35 U.S.C. 154(b) by 0 days.

(21) Appl. No.: 10/474,332

(22) PCT Filed: Apr. 11, 2002

(86) PCT No.: PCT/FR02/01269

§ 371 (c)(1),
(2), (4) Date: Apr. 23, 2004

(87) PCT Pub. No.: WO02/085085

PCT Pub. Date: Oct. 24, 2002

(65) Prior Publication Data
US 2004/0163841 A1     Aug. 26, 2004

(30) Foreign Application Priority Data
Apr. 12, 2001  (FR) .................................. 01 05053

(51) Int. Cl.
*H01R 12/00* (2006.01)
*H05K 1/00* (2006.01)

(52) U.S. Cl. ........................................................ 439/67

(58) Field of Classification Search ................. 439/67; 174/88 R
See application file for complete search history.

(56) References Cited

U.S. PATENT DOCUMENTS

| | | | |
|---|---|---|---|
| 4,538,143 A | 8/1985 | Ito | 340/719 |
| 4,815,990 A | 3/1989 | Ristedt et al. | 439/496 |
| 5,260,518 A | 11/1993 | Tanaka et al. | 174/261 |
| 6,245,047 B1 * | 6/2001 | Feda et al. | 604/192 |

FOREIGN PATENT DOCUMENTS

| | | |
|---|---|---|
| DE | 43 27 560 A1 | 2/1995 |
| DE | 195 30 353 A1 | 2/1997 |
| JP | 09276236 | 10/1997 |
| JP | 09312453 | 12/1997 |

* cited by examiner

*Primary Examiner*—Javaid H. Nasri
(74) *Attorney, Agent, or Firm*—Duane Morris LLP

(57) ABSTRACT

The invention concerns a method for connecting first contact studs of a structure bearing electrodes for measuring or for stimulating a physiological activity with second studs of at least a downstream circuit, each second stud being traversed by an opening perforating the downstream circuit. The method includes the following steps: a) placing the downstream circuit on the structure, so that the opening of a second stud is located opposite a first stud; and b) depositing in the opening of the second stud a conductive material providing the connection between the first second stud opposite.

28 Claims, 4 Drawing Sheets

CONNECTING METHOD FOR STRUCTURE WITH IMPLANTABLE ELECTRODES

FIELD OF THE INVENTION

The present invention relates to structures supporting electrodes intended to measure the electric activity of an organ or to stimulate it, and in particular to the connection of these structures to a circuit.

BACKGROUND OF THE INVENTION

In FIG. 1, a structure 1 with electrodes is intended to be connected to a downstream circuit 2. Structure 1 comprises an insulating flexible support film 3. On film 3 are deposited electrodes 4 connected by conductive tracks 5 to connection pads 6. The electrodes, the pads, and the tracks connecting them are formed by deposition and etching of a conductive layer on film 3. A thin insulating layer, not shown, covers the structure, except for the electrodes and the pads. Structure 1 is a flexible structure of small thickness (from a few micrometers to a few tens of micrometers), the electrodes of which are intended to be placed to contact an organ such as a nerve or the skin to measure the electric activity of the organ or to stimulate it.

Structure 1 must be connected to circuit 2. Circuit 2 comprises pads 7, the arrangement of which corresponds to that of pads 6. Each pad 7 is connected to a conductive track 8 for the conduction of the signal provided to or by electrodes 4. To connect a pad 6 to a pad 7, a hole 10 thoroughly crossing the structure is made in each of pads 6.

In FIG. 2, downstream circuit 2 is partially shown and a single contact pad 7 is visible. Structure 1 is here shown with support film 3, a single pad 6, and an upper insulating layer 11. The thickness of circuit 2, on the order of from one to two millimeters, is significant as compared to that of structure 1, which is at most a few tens of micrometers. Structure 1 is placed on circuit 2 so that each of holes 10 is above a pad 7. The surface of each pad 7 is greater than that of a hole 10. A welding drop 12 is then deposited, by a conventional bonding technique well known in microelectronics, which fills hole 10 and overflows on pad 6. Welding drop 12 ensures the electric contact between pads 6 and 7.

This way of doing has several disadvantages.

The electrode-supporting structure must be drilled into in the middle of each pad 6. This operation is delicate, due to the fragility of the structure, and this assumes that pads 6 are large enough, which limits their number. The drilling of pads 6 is generally performed by means of a laser beam, which results in having the metal layer forming the pad partially split, so that the pad no longer exhibits a uniform surface. The drilling of pads 0.6 may also be carried out by etching, which requires an additional mask, which brings about a cost problem, and greatly increases the pad drilling time.

Further, the impedance exhibited by this type of contact is relatively high. Indeed, the surface of pad 6 enabling flowing of an electric signal between pads 6 and 7 is a substantially ring-shaped surface 13 delimited by the base of welding drop 12 and the circumference of hole 10. The surface of pad 7 enabling flowing of the electric signal is a substantially circular surface 14 equal to the surface area of hole 10. Surfaces 13 and 14 have been shown in bold lines in FIG. 2. To avoid too much decreasing the impedance of the contact between pads 6 and 7, surfaces areas 13 and 14 must be substantially equal. As a result, at most, the surface area enabling flowing of an electric current between pads 6 and 7 is equal to half the surface area of pad 6, which makes the impedance of the contact between pads 6 and 7 relatively high.

Further, welding 12 forms a brittle dome of relatively great height, typically on the order of 50 micrometers. This may hinder the circuit encapsulation.

German patent application DE 19530353 A1 generally describes a method for connecting contact areas of a flexible film to a printed circuit. In this document, the printed circuit has pads drilled with metallized holes, the metallization extending somewhat over the rear surface of the integrated circuit which does not support the pads. The portions of the film and of the circuit to be connected are opposite and a filler metal is deposited between them. Heat is provided to the rear circuit surface, while a relatively high pressure is applied on the assembly formed by the film and the circuit. The provided heat melts the filler metal, which forms a relatively thick gluing layer between the film and the circuit. The excess filler metal is absorbed by the metallized hole.

The abstract of Japanese patent JP 09312453 describes a technique similar to that described in application DE 19530353.

The techniques described in the two above documents require application of a high temperature and pressure. When such techniques are desired to be applied to connect a structure support electrodes intended to measure the electric activity of an organ or to stimulate it, several problems arise. Indeed, electrode structures are very thin and very brittle. The application of a pressure, even mild, crushes the structure and may damage it. Further, the application of a high temperature, necessary to melt the filler metal, may destroy the structure. It will be seen hereafter that the overthickness created by the welding layer may also be a disadvantage.

SUMMARY OF THE INVENTION

An object of the present invention is to form a connection between an electrode structure intended to measure or stimulate an activity of physiological origin and a circuit, without for a high pressure to be exerted between the parts to be connected.

Another object of the present invention is to form a connection between an electrode structure intended to measure or to stimulate an activity of physiological origin and a circuit, without for a high temperature to be applied to one of the parts to be connected.

Another object of the present invention is to form an easy connection between an electrode structure intended to measure or to stimulate an activity of physiological origin and a circuit.

Another object of the present invention is to form a connection enabling optimization of the contact impedance between an electrode structure intended to measure or to stimulate an activity of physiological origin and a circuit.

Another object of the present invention is to form a substantially planar connection between an electrode structure intended to measure or to stimulate an activity of physiological origin and a circuit.

Another object of the present invention is to form a connection between an electrode structure intended to measure or to stimulate an activity of physiological origin and a circuit enabling optimal use of the surface area of the structure and/or of the circuit.

To achieve these and other objects, the present invention provides a method for connecting first pads of an electrode-supporting structure capable of measuring or of stimulating an activity of physiological origin to second pads of at least one downstream circuit, each second pad being run through by an opening perforating the downstream circuit, comprising the steps of:

a) placing the downstream circuit on said structure, so that the opening of the second pad is placed opposite to a first pad; and b) depositing in the opening of the second pad a conductive material ensuring the connection between the second pad and the first opposite pad.

According to an embodiment of the present invention, the opening made in the second pad has a surface area substantially equal to the surface area of the first opposite pad.

According to an embodiment of the present invention, the portion of said structure comprising the first pads is cut to form blade terminals, and the connection of the second pads to the first pads is such that the first pads of two adjacent blade terminals at least are connected to second pads of different downstream circuits, arranged substantially one above another.

According to an embodiment of the present invention, the opening perforating the downstream circuit is a metallized hole.

According to an embodiment of the present invention, the connection of the first pads to the second pads is made by means of a conductor glue, of a conductor paste, or of a welding.

According to an embodiment of the present invention, the second pad has a thickness on the order of from 20 to 50 micrometers and the first pad has a thickness equal to at most a few micrometers.

The present invention also provides a structure supporting electrodes capable of measuring or of stimulating an activity of physiological origin exhibiting first pads likely to be connected to second pads of downstream circuits by a method according to the present invention. The portion of said structure comprising the first pads is cut to form blade terminals each supporting first pads.

The present invention also provides a structure supporting electrodes capable of measuring or of stimulating an activity of physiological origin exhibiting first pads that can be connected to second pads of at least one downstream circuit by a method according to the present invention, the first pads being connected to the electrodes by conductive tracks. Said conductive tracks are arranged on at least two superposed levels separated by insulating layers, and at least one conductive track runs under a first pad.

The present invention also provides an assembly formed of a structure supporting electrodes capable of measuring or of stimulating an activity of physiological origin and a downstream circuit, wherein the electrode-supporting structure and the downstream circuit are connected by an above method.

In an embodiment of the present invention, the portion of the electrode-supporting structure that comprises pads and at least the portion of the downstream circuit that is connected to said structure are covered with a biocompatible sheath.

BRIEF DESCRIPTION OF THE DRAWINGS

The foregoing objects, features, and advantages of the present invention will be discussed in detail in the following non-limiting description of specific embodiments in connection with the accompanying drawings, in which.

In the drawings, same reference numerals represent same elements. The scales have not been respected, especially regarding thicknesses.

DETAILED DESCRIPTION OF THE INVENTION

Figure 3A:
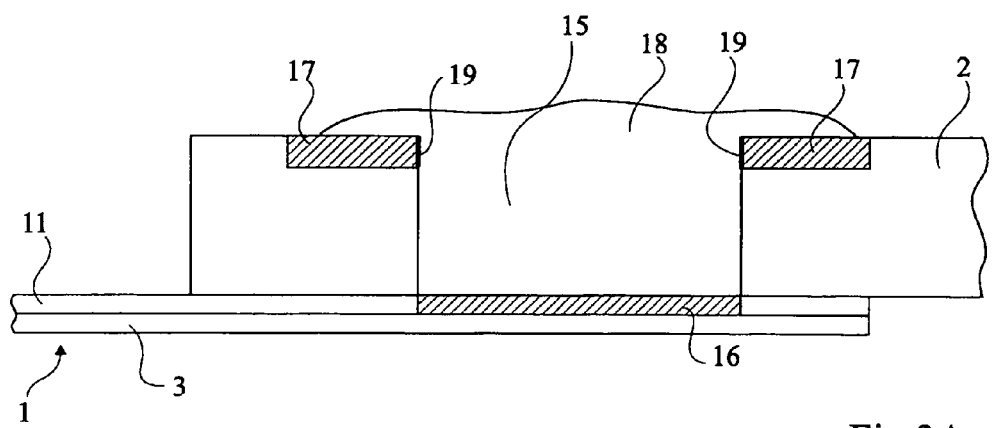
FIG. 3A shows the connection of an electrode structure and of a downstream circuit according to a first embodiment of the present invention.

FIG. 3A shows a first embodiment of the present invention. The end of an electrode structure 1 of the above-mentioned type comprises an insulating support film 3, a pad 16, and an upper insulating layer 11. A circuit 2 comprising a pad 17 to be connected to pad 16 is here placed above structure 1. Circuit 2 comprises an opening 15 which completely crosses it, substantially located at the center of pad 17. In the example shown, opening 15 has a size substantially equal to that of pad 16. Opening 15 is filled with a material 18 ensuring the electric connection of pads 16 and 17. Material 18 is preferably a conductive paste or glue, but it may also be a welding. For example, a drop of conductive glue is deposited in opening 15 and set by means of ultraviolet rays. Material 18 fills opening 15 and has a substantially planar surface which very slightly extends beyond the surface of circuit 2.

Figure 1:
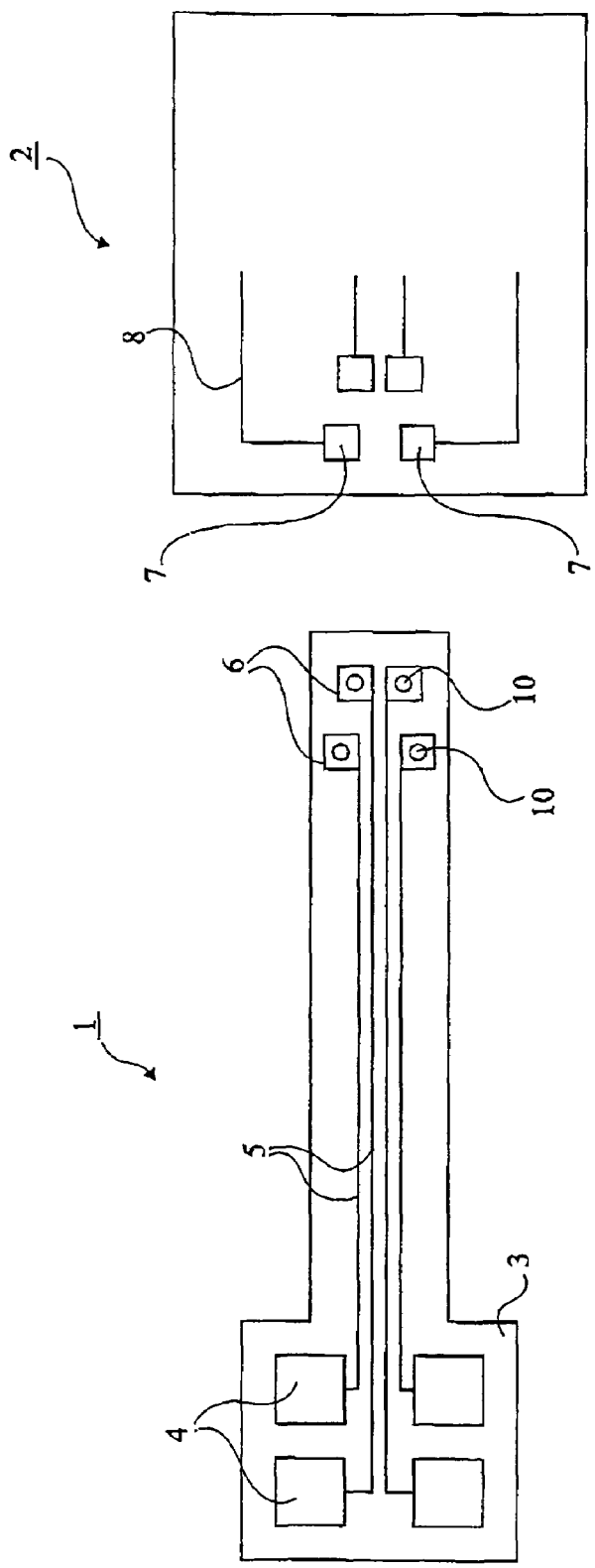
FIG. 1, previously described, shows an electrode structure and a downstream circuit.
Figure 2:
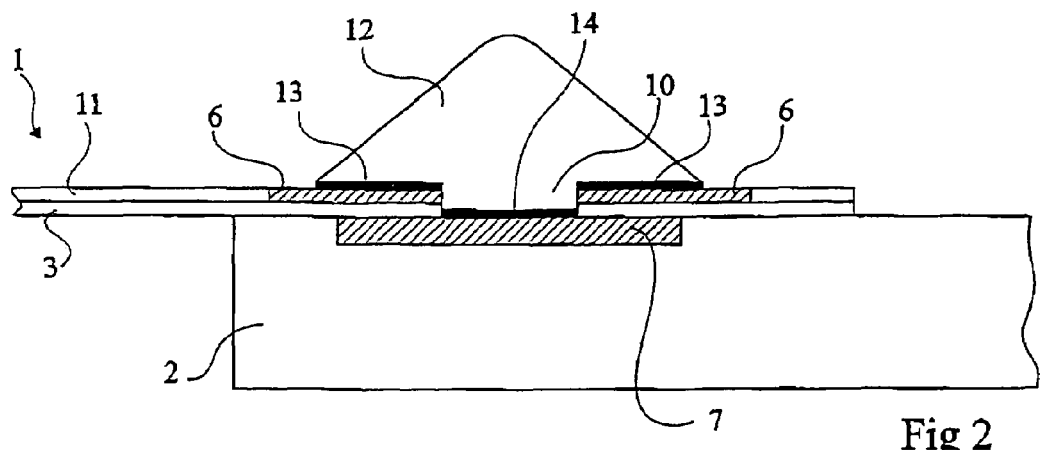
FIG. 2 shows a known type of connection between an electrode structure and a downstream circuit.

According to the present invention, circuit 2 is placed above structure 1, rather than the opposite as in FIG. 2. This has many advantages.

First, in the present invention, the drilling is performed in circuit 2 and not in structure 1. Now, circuit 2 is generally much thicker than structure 1 (typically a hundred times as thick) and it is much easier to regularly drill into circuit 2 than structure 1. Further, the conductive layer forming pads 17 often is much thicker than the conductive layer forming pads 16, and it is accordingly much less brittle (typically, the thickness of a pad 17 is on the order of from 20 to 50 micrometers while the thickness of a pad 16 is of a few micrometers at most, or even under one micrometer). The holes of circuit 2 may be formed by means of various techniques, like by means of conventional mechanical drilling techniques, and they are more regular. The holes of circuit 2 may also be formed before deposition of the conductive layer forming pads 17. This enables, for example, using a laser beam drilling without risking to damage pads 17.

Further, the fact that the thickness of pad 17 is generally much greater than that of pad 16 plays a role for the connection impedance. Indeed, the surface area of cylindrical crown 19 (in bold lines in FIG. 3A) corresponding, in opening 15, to the thickness of pad 17, is significant and non-negligibly takes part in the flowing of the electric current. As an example, it is assumed that pads 16 and 17 have a same radius R and that thickness e of pad 17 is also equal to R. If an opening 15 that represents 75% of the surface area of pad 17 is selected, the surface area of pad 16 taking part in the current conduction is $0.75.\pi R^2$. Cylindrical surface 19 represents, as for itself, approximately $1.7.\pi Re$, and thus $1.7.\pi R^2$, that is, twice as much. Since pads 16 and 17 generally have a small radius (typically some ten micrometers), thickness e is generally greater than the pad radius and, as concerns pad 17, it is the thickness which mainly takes part in the current flowing. As a result, connection material 18 needs not widely extend over pad 17 and pad 17 needs not have a large surface area, which optimizes the used surface area. Further, if need be, material 18 may significantly overflow over the conductive layer which, in circuit 2, leads to pad 17. Also, pad 17 may, if desired, be simply formed by a portion of a conductive track of circuit 2, pierced by an opening 15.

Further, in the present invention, connection material 18 fills the hole defined by opening 15, which generally is a deep hole, conversely to hole 10 of FIG. 2. As a result, a sufficient quantity of conductive material is systematically used and forms strong connections, without forming a significant dome as in FIG. 2. It should further be noted that it is possible to scrape material 18 from the surface of circuit 2 and obtain a practically planar surface of circuit 2.

As compared to the connections described in documents DE 19530353 and JP 09312453, the connection of FIG. 3A has required no application of an excessive pressure or heat. Indeed, structure 1 and circuit 2 are simply placed against each other during the connection and maintained in place with no excessive pressure during the connection. If need be, structure 1 may be glued to circuit 2 by means of a thin insulating layer of insulating glue which does not cover pads 16.

Figure 3B:
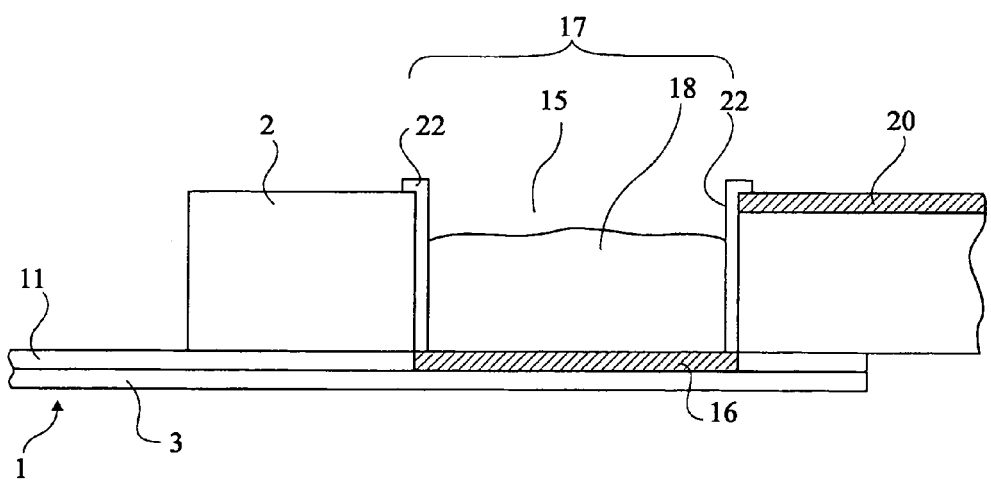
FIG. 3B shows the connection of an electrode structure and of a downstream circuit according to a second embodiment of the present invention.

FIG. 3B shows a second embodiment of the present invention. In FIG. 3B, a conductive track 20 of circuit 2 ends on opening 15 of pad 17. The hole defined by opening 15 is metallized. A conductive layer 22 covers the walls of opening 15. Layer 22 may, as shown, slightly overflow over the surface of circuit 2, but this is not necessary. Pad 17 is thus defined by conductive layer 22, connected to track 20. In this embodiment, the surface area of pad 17 taking part in the electric current conduction is very large. Connection material 18 needs not fill the entire opening 15 to ensure a good mechanical strength and a good conduction of the connection. The surface of circuit 2 remains planar. This embodiment enables particularly significant decrease in the impedance of the formed connection and pad 17 takes up no more space than opposite pad 16. This is a significant advantage, especially when many pads 16 are arranged on a reduced surface of structure 1.

Figure 4A:
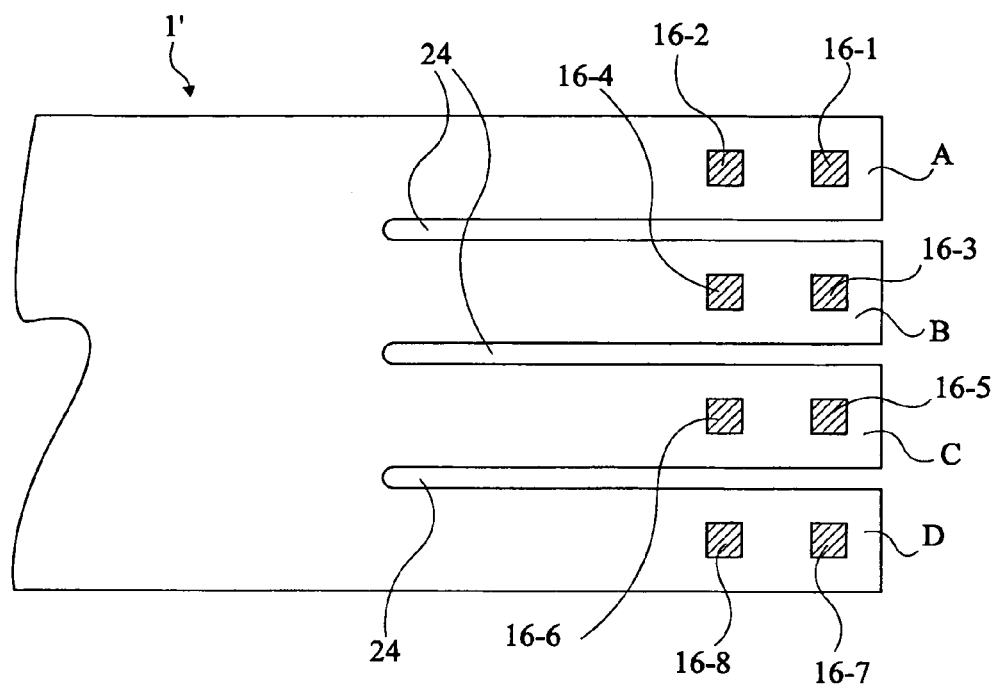
FIGS. 4A and 4B respectively show a novel electrode structure and its mode of connection to a downstream circuit according to a third embodiment of the present invention.
Figure 4B:
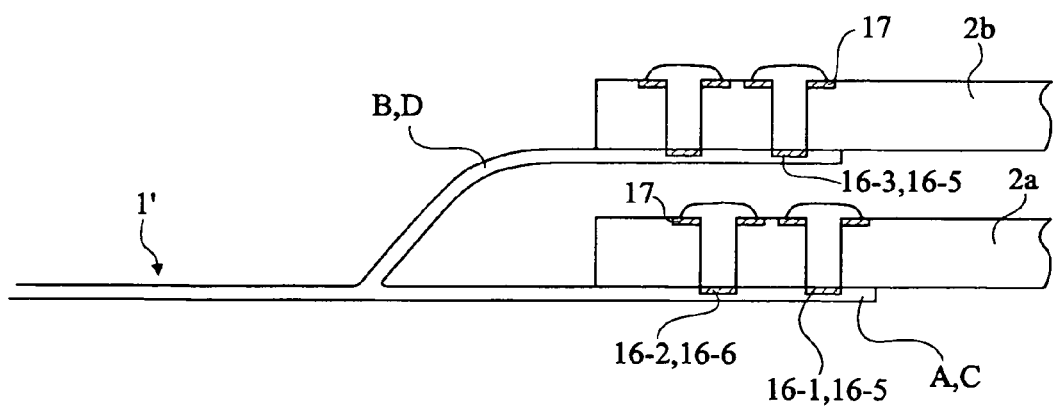

FIGS. 4A and 4B illustrate a third embodiment of the present invention, which enables a great versatility, and forming pads 17 of large size.

FIG. 4A shows a novel structure of electrodes 1'. In FIG. 4A, the end of structure 1' comprises eight pads 16-$i$, with i ranging from 1 to 8. The end of the structure is cut by three longitudinal openings 24 separating pads 16-$i$ in groups of two. Openings 24 thus divide the end of structure 1' into four longitudinal blade terminals A, B, C, D, arranged in this order and comprising two pads each.

FIG. 4B illustrates the way of connecting structure 1'. Structure 1' is connected to two downstream circuits 2a and 2b. Non-adjacent blade terminals A and C are connected to circuit 2a in the way described in relation with FIG. 3A or 3B. Similarly, non-adjacent blade terminals B and D are connected to circuit 2b in the way described in relation with FIG. 3A or 3B.

Circuits 2a and 2b are arranged one above the other. The insulating support film of structure 1 may by itself ensure the electric insulation between circuits 2a and 2b, or an additional insulator such as an insulating sheet will separate circuits 2a and 2b.

By so operating, a stacking of circuits 2a and 2b is formed. Pads 17 of each of circuits 2a or 2b may have a surface area which is double that of pads 16-$i$ and extend over the width of two blade terminals A, B, C, D. Thus, for example, pad 17 connected to pad 16-1 of blade terminal A may take up a surface area corresponding to pad 16-1 and to pad 16-3 of blade terminal B. It will easily exhibit an opening 15 of same surface area as pad 16-1.

This connection mode is advantageous. For example, the pads of structure 1' may be twice as small and thus twice as many as in prior art, or the width of structure 1' may be twice as small. The obtained assembly forms a very versatile compact assembly, practical to arrange. "Circuits 2a and 2b" is used to designate either two separate downstream circuits, coupled or not, or merely two superposed elements of a multiple-stage three-dimensional connector, associated with a single downstream circuit.

Of course, the present invention is likely to have various alterations, modifications, and improvements which will readily appear to those skilled in the art. In particular, the electrode-supporting structure has been described as having an elongated shape, with electrodes at one end and pads at the other end. However, the structure may have any shape, for example, a circular shape, and the electrodes and pads of the structure may be arranged in any part of the structure. Also, the pads may be in any number in the structure, for example, as many as several hundreds.

It should be noted that the connection method of the present invention applies for a diversity of thicknesses of the electrode-supporting structure and of circuit 2.

It should also be noted that pads 17 may have any shape.

Also, in the connection mode illustrated in relation with FIGS. 4A and 4B, the structure may be cut into a number of blade terminals different from four and the number of downstream circuits or of superposed elements of a connector of the down-stream circuit may be greater than two. Also, even though each of the blade terminals of FIG. 4A is shown with a single row of pads, the blade terminals may comprise several rows of pads, for example, two. Also, it is not necessary for all adjacent blade terminals to be connected to different downstream circuits. For example, blade terminals A and D of FIG. 4B may be connected to circuit 2a and blade terminals B and C to circuit 2b, providing the same advantages as those mentioned in relation with FIG. 4B.

It should also be noted that other advantages of the connection method according to the present invention will occur to those skilled in the art. For example, in the case where the structure comprises not one electrode layer, but several, the present invention has a significant advantage.

Figure 5:
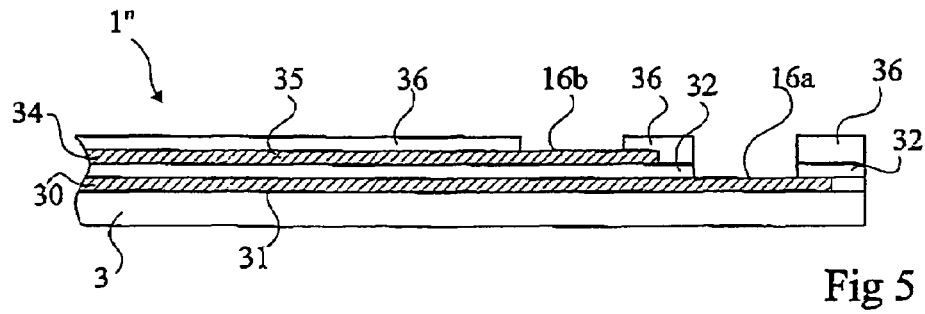
FIG. 5 shows a novel electrode structure illustrating an advantage of the connection according to the present invention.

FIG. 5 shows a structure 1" with two electrode layers. Support film 3 of structure 1" is covered with a first conductive layer 30. Layer 30 is etched to form, at one end of the structure, a pad 16a connected by a conductive track 31 to an electrode not shown. On layer 30 is an insulating layer 32. On layer 32 is arranged a second conductive layer 34. Layer 34 is etched to form a pad 16b, connected by a conductive track 35 to an electrode not shown. Layer 34 is topped with an insulating layer 36. Layers 32 and 36 are properly etched to expose pads 16a and 16b. Pad 16a and track 31 are located at a level lower than pad 16b and track 35. In prior art, as described in relation with FIG. 2, since pads 16a and 16b must be drilled into with perforating holes, layer 31 cannot be located under pad 16b, unless track 31 follows a complicated path and a complex mask is used to etch it. The surface area required to form track 31 may then be relatively large. In the present invention, track 31 may run under pad 16b and be rectilinear. The structure surface is better used and the mask used for the etching of layer 31 is simpler.

Finally, the connection according to the present invention may have various applications. For example, as illustrated in FIG. 6, the electrode structure may be connected to another flexible structure, and not to a rigid downstream circuit.

Figure 6:
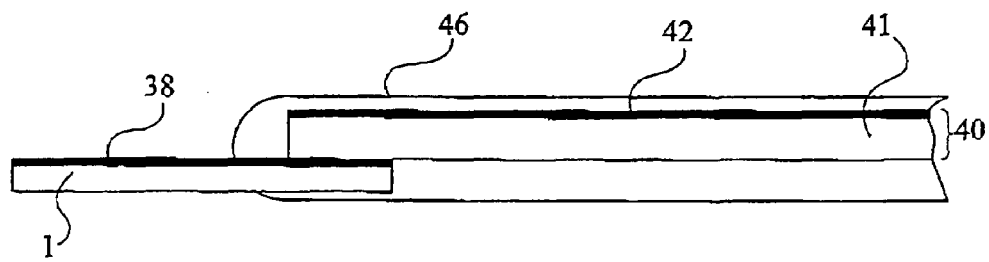
FIGS. 6 and 7 show examples of application of a connection according to the present invention.

In FIG. 6, an electrode structure 1 having its layer 38 supporting electrodes and connection pads shown in bold lines, is connected to a flexible film 40, playing the role of a downstream circuit. Film 40 comprises an insulating base 41 and, at its upper surface, a conductive layer 42 in which are formed the pads to be connected to the pads of layer 38. The connection between structure 1 and pad 40 is formed by means of the connection method according to the present invention, and the pads of structure 1 and of film 40 are not shown for simplicity. A biocompatible sheath 46 surrounds film 40, or at least the portion of film 40 intended to contact one or several organs, and the portion of structure 1 comprising the pads.

The example of FIG. 6 is particularly advantageous. Indeed, structure 1, to be placed at the contact of an organ, is biocompatible and its selfcost is high. Further, the manufacturing of structure 1 is performed by deposition of layers on a mother wafer, and it is advantageous to simultaneously form the largest possible number thereof. Thus, it is advantageous to form relatively short structures 1 (typically, on the order of 2 centimeters). Now, in certain applications, the organ to be tested or stimulated is at a non-negligible depth of the body surface. For example, in surgery of the base of the skull (retrosigmoid approach), the acoustic nerve is located at a 5-centimeter depth and a short electrode structure does not reach it. In FIG. 6, the assembly formed by structure 1 and film 40 may be relatively long, for example, it may reach 20 cm, and biocompatible sheath 46 enables introduction of the assembly to the desired depth. Further, the assembly of FIG. 6 is relatively inexpensive. Indeed, the materials covered by the biocompatible sheath need not be biocompatible and have a lesser cost.

In the example of FIG. 6, it is advantageous to keep the thickness of the assembly formed by structure 1 and film 40 as small as possible. With the connection method according to the present invention, structure 1 and film 40 may be arranged directly against each other, with no gluing layer in between, the pads of structure 1 and of film 40 being on opposite surfaces. This is an advantage with respect to previously-mentioned prior art documents DE 19530353 and JP 09312453. Indeed, in these two documents, the pads to be interconnected face one another, conversely to the present invention, and a welding layer forming a relatively thick gluing layer is present between the thin structure and the thick structure. In the present invention, if for example a structure from 1 to 3 microns and a 20-micron film 40 are used, the assembly of structure 1 and of film 40 has a 23-micron thickness. The addition of a bonding layer, as in documents DE 19530353 and JP 09312453, between structure 1 and film 40, would considerably increase the thickness of the assembly formed by the structure and the film, which can make it inoperative in certain applications. Further, the presence of a rigid and brittle gluing layer may be a disadvantage (lack of flexibility, risk of connection breakage). Moreover, the fact that, in the present invention, the surface of the structure comprising the pads faces the surface of the downstream circuit devoid of pads leaves the surface of the downstream circuit comprising the pads free. This enables, for example, the downstream circuit to comprise many pads and many connection tracks without risking for these to form undesired contacts with the structure pads and/or tracks.

Figure 7:
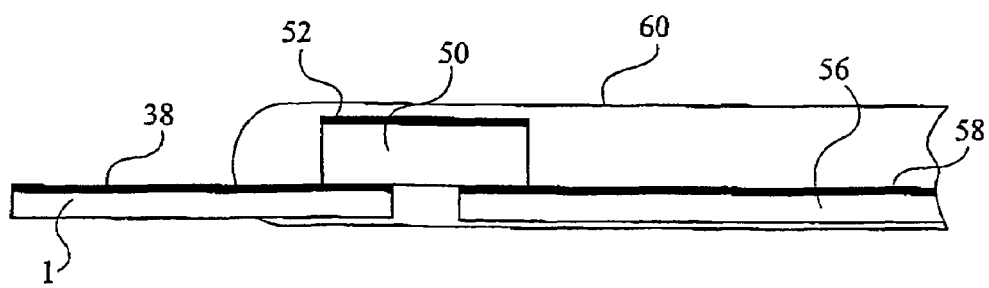

FIG. 7 illustrates another example of application of the connection method according to the present invention. In FIG. 7, an electrode structure 1, having a layer 38 supporting electrodes and connection pads, is connected to one end of a rigid element 50 supporting, on its upper surface 52, connection pads and metal tracks. The other end of rigid element 50 is connected to a flexible film of small thickness 56, which supports connection pads on its upper surface 58. The connections between rigid element 50 and, respectively, structure 1 and film 56, are formed according to the method of the present invention. Rigid element 50 may be relatively short, for example, 5 mm. A biocompatible sheath 60 surrounds film 56, rigid element 50 and the portion of structure 1 supporting the pads. As in FIG. 6, sheath 60 enables connecting structure 1 to a relatively long flexible film, the assembly being biocompatible and relatively inexpensive. Element 50 may have various functions. For example, the surgeon may seize it by means of pliers to more easily introduce the structure. Element 50 may also be used, after the placing of the structure, to attach the assembly to the operating theatre napkin. Element 50 needs not be made of a biocompatible material. It may have various thicknesses, for example, on the order of 50 micrometers. Further, the masks of manufacturing of element 50 need not be as accurate as those used in the manufacturing of structure 1 and they are accordingly less expensive.

It has already been signaled that no high pressure needs be exerted for the connection according to the present invention of an electrode structure to a downstream circuit. This is particularly advantageous in certain cases, for example, where the electrode structure exhibits protruding elements at the pads, for example, elements having a 20-micron thickness or more, made of a relatively soft insulating material, which would crush upon application of a high voltage.

Finally, it should be noted that the electrode structures described in relation with FIGS. 4A and 5 may also be connected by any other method without departing from the scope of the present invention. Also, an electrode structure resulting from a combination of the structures of FIGS. 4A and 5, for example, a structure in which one or several blade terminals comprise pads connected to superposed tracks, is part of the present invention.

The invention claimed is:

1. A device comprising:
   a bio-compatible film structure comprising at least one electrode for measuring or stimulating an activity of physiological origin, at least one first pad, and at least one track, the at least one track coupling the at least one electrode to the at least one first pad, the film structure further having a thickness;
   at least one downstream circuit having a thickness greater than the thickness of said film structure and comprising at least one second pad having an opening perforating the downstream circuit, the downstream circuit being located on said structure so that the surface of the downstream circuit devoid of the at least one second pad is in contact with the structure and so that the opening of the at least one second pad is placed opposite to the at least one first pad;
   wherein said structure is linked to said downstream circuit by a conductive material located in the opening of the at least one second pad thus ensuring the connection between the at least one second pad and the at least one first pad.

2. The device of claim 1, wherein said film structure thickness is less than about 10 micrometers.

3. The device of claim 1, wherein said film structure has a thickness of about 8 micrometers.

4. The device of claim 1, wherein said downstream circuit has a thickness greater than about 20 micrometers.

5. The device of claim 1, wherein said downstream circuit has a thickness of about 85 micrometers.

6. The device of claim 1, wherein the at least one first pad has a thickness less than about 10 micrometers.

7. The device of claim 1, wherein the at least one first pad has a thickness less than 1 micrometer.

8. The device of claim 1, wherein the at least one first pad 30 has a thickness of about 0.1 micrometer.

9. The device of claim 1, wherein the at least one second pad his a thickness of from about 20 to about 50 micrometers.

10. The device of claim 1, wherein the at least one second pad has a thickness of about 35 micrometers.

11. The device of claim 1, wherein the portion of said film structure comprising the at least one first pad and at least the portion of the downstream circuit that is connected to said film stricture are covered with a biocompatible sheath.

12. The device of claim 1, wherein said conductive material is a conductive glue.

13. The device of claim 1, wherein said conductive material is a conductive paste.

14. The device of claim 1, wherein said conductive material comprises weld metal.

15. The device of claim 1, wherein the size of said first pad is less than about 1 mm$^2$.

16. The device of claim 1, wherein the opening in the at least one second pad has a surface area substantially equal to the surface area of the at least one first pad.

17. The device of claim 1, wherein the opening perforating the downstream circuit is a metallized hole.

18. The device of claim 1, wherein the portion of said film structure comprising the at least one first pad comprises blade terminals, the at least one downstream circuit comprises a pair of downstream circuits, the at least one first pad comprises a pair of first pads and the at least one second pad comprises a pair of second pads each connected to a different one of the pair of downstream circuits, and wherein a connection between one of the pair of second pads to one of the pair of first pads is such that the pair of first pads are located on adjacent blade terminals and are ranged substantially one above another.

19. The device of claim 1, wherein the at least one track comprises a pair of tracks, the at least one first pad comprises a pair of first pads, and the at least one electrode comprises a pair of electrodes, wherein each of the pair of electrodes is arranged on a separate superposed level, the levels being separated by at least one insulating layer, and wherein at least one of the pair of conductive tracks runs under one of the first pads.

20. The device of claim 1, wherein the film structure supporting electrodes for measuring or stimulating an activity of physiological origin comprises a plurality of first pads connected to a plurality of second pads of at least one downstream circuit, wherein the portion of said structure comprising the plurality of first pads comprises separate blade terminals, each blade terminal supporting at least one first pad.

21. The device of claim 1, wherein the film structure supporting electrodes for measuring or stimulating an activity of physiological origin comprises a plurality of first pads for connecting to a plurality of second pads of at least one downstream circuit, the plurality of first pads being connected to the electrodes by a plurality of conductive tracks, wherein said plurality of conductive tracks arc arranged on at least two superposed levels separated by at least one insulating layer.

22. The device of claim 1, wherein the film structure supporting electrodes for measuring or stimulating an activity of physiological origin comprises a plurality of first pads for connecting to a plurality of second pads of at least one downstream circuit, the plurality of first pads being connected to the electrodes by a plurality of conductive tracks, wherein said plurality of conductive tracks are arranged on at least two superposed levels separated by at least one insulating layer, and wherein at least one of the plurality of conductive tracks runs under at least one of the plurality of first pads.

23. A method for connecting a first pad of a structure supporting one or more electrodes for measuring or stimulating an activity of physiological origin to a second pad of at least one downstream circuit, said downstream circuit having a thickness that is greater than a thickness of said structure, said second pad having an opening perforating the downstream circuit the method comprising the steps of:
   a) placing the downstream circuit on said structure, so that to surface of the downstream circuit devoid of said second pad is in contact wit the structure and the opening of said second pad is placed opposite to said first pad; and
   b) depositing in the opening of said second pad a conductive material to connect said second pad to said first pad.

24. The method of claim 23, wherein the opening made in said second pad has a surface area substantially equal to a surface area of said first pad.

25. The method of claim 23, wherein the structure comprises a plurality of first pads for connection with a respective plurality of second pads of at least two downstream circuits, and the portion of said structure comprising said plurality of first pads is cut to form blade terminals, and wherein the first pads associated with adjacent blade terminals are connected to respective second pads of different downstream circuits and the first pads are arranged substantially one above another.

26. The method of claim 23, wherein the opening perforating the downstream circuit is a metallized hole.

27. The method of claim 23, wherein the first and second pads are connected using conductive glue, conductive paste, or weld metal.

28. The method of claim 23, wherein the second pad has a thickness of from about 20 to about 50 micrometers and the first pad has a thickness less than about 10 micrometers.

* * * * *